(12) United States Patent
Sniadach

(10) Patent No.: US 6,718,970 B2
(45) Date of Patent: Apr. 13, 2004

(54) INTUBATION SYSTEM AND METHODS OF USE THEREOF

(76) Inventor: Joseph A. Sniadach, 4427 Wynn Rd., Baltimore, MD (US) 21236

( * ) Notice: Subject to any disclaimer, the term of this patent is extended or adjusted under 35 U.S.C. 154(b) by 0 days.

(21) Appl. No.: 09/912,699

(22) Filed: Jul. 25, 2001

(65) Prior Publication Data

US 2003/0062039 A1 Apr. 3, 2003

(51) Int. Cl.$^7$ .............................................. A61M 16/00
(52) U.S. Cl. .............................. 128/200.26; 128/207.14
(58) Field of Search ........................ 128/200.26, 207.14, 128/207.15, 207.29

(56) References Cited

U.S. PATENT DOCUMENTS

| | | | | |
|---|---|---|---|---|
| 3,968,800 A | * | 7/1976 | Vilasi .................... | 128/207.14 |
| 4,825,858 A | | 5/1989 | Frankel ................. | 128/200.26 |
| 4,832,020 A | * | 5/1989 | Augustine ............. | 128/207.14 |
| 4,865,586 A | | 9/1989 | Hedberg ............... | 604/93 |
| 5,024,218 A | | 6/1991 | Ovassapian et al. ... | 128/200.26 |
| 5,042,469 A | | 8/1991 | Augustine ............. | 128/200.26 |
| 5,058,580 A | * | 10/1991 | Hazard .................. | 128/200.26 |
| 5,174,283 A | | 12/1992 | Parker .................. | 128/200.26 |
| 5,188,100 A | * | 2/1993 | Miles et al. ........... | 128/200.26 |
| 5,203,320 A | * | 4/1993 | Augustine .............. | 600/187 |
| 5,353,787 A | | 10/1994 | Price ..................... | 128/200.26 |
| 5,372,131 A | | 12/1994 | Heinen, Jr. ............ | 128/207.15 |
| 5,507,279 A | * | 4/1996 | Fortune et al. ........ | 128/200.26 |
| 5,694,929 A | | 12/1997 | Christopher ........... | 128/207.14 |
| 5,791,338 A | * | 8/1998 | Merchant et al. ...... | 128/200.26 |
| 5,791,341 A | * | 8/1998 | Bullard ................. | 128/200.26 |
| 5,850,832 A | * | 12/1998 | Chu ...................... | 128/200.26 |
| 6,053,166 A | | 4/2000 | Gomez .................. | 128/200.26 |
| 6,286,509 B1 | * | 9/2001 | Nash et al. ............ | 128/200.26 |

* cited by examiner

*Primary Examiner*—Aaron J. Lewis
*Assistant Examiner*—Mital Patel
(74) *Attorney, Agent, or Firm*—J. Bruce Hoofnagle

(57) ABSTRACT

An intubation system for intubating a patient includes an esophageal obturator 10, an intubation slide 30, a directing guide wire assembly 48 and an airway tube 60. In a method for obtaining an unobstructed airway into the patient's lungs, the esophageal obturator 10 is used to occlude the patient's esophagus F. The intubation slide 30 is inserted into the patient's mouth C and provides a guide for a directing guide wire 50 of the assembly 48 to locate a distal end 59 of the wire in the patient's trachea E. A distal end of the airway tube 60, which surrounds, or may be slipped over, the emplaced assembly 48, is also thereby located in the patient's trachea E. The obturator 10, the slide 30 and the assembly 48 are removed, thereby leaving the airway tube 60 in place to provide ventilation for the patient.

21 Claims, 13 Drawing Sheets

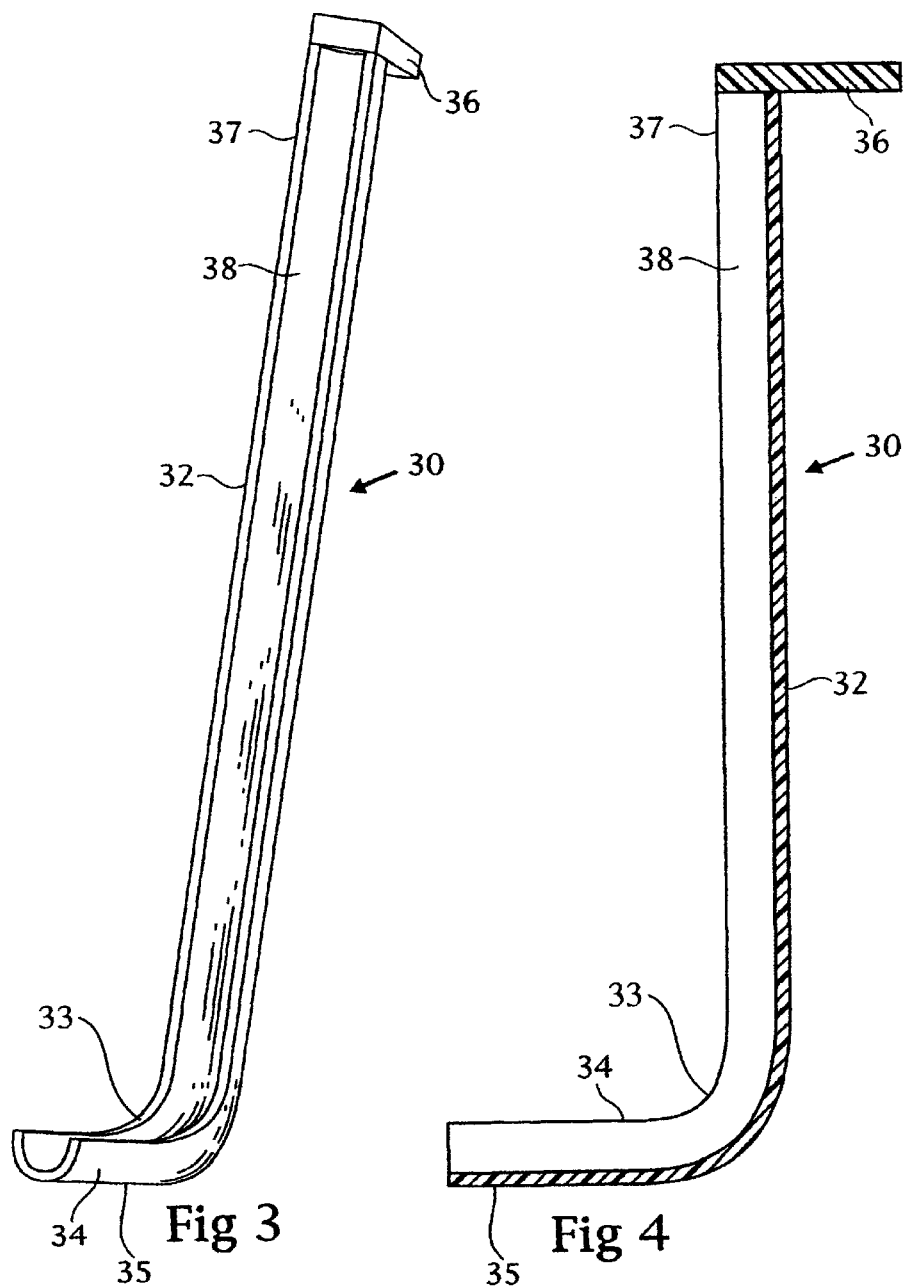

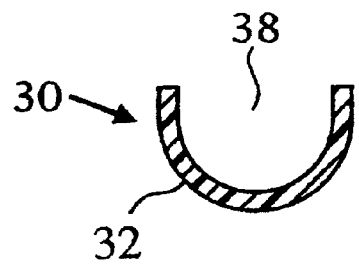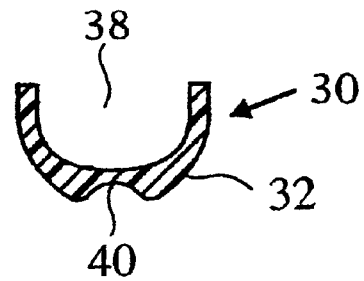
Fig 7   Fig 8
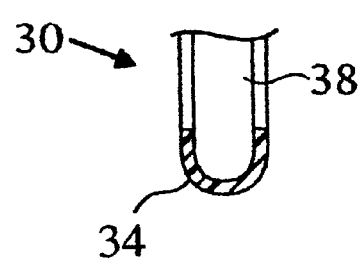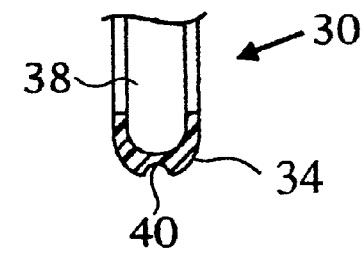
Fig 9   Fig 10

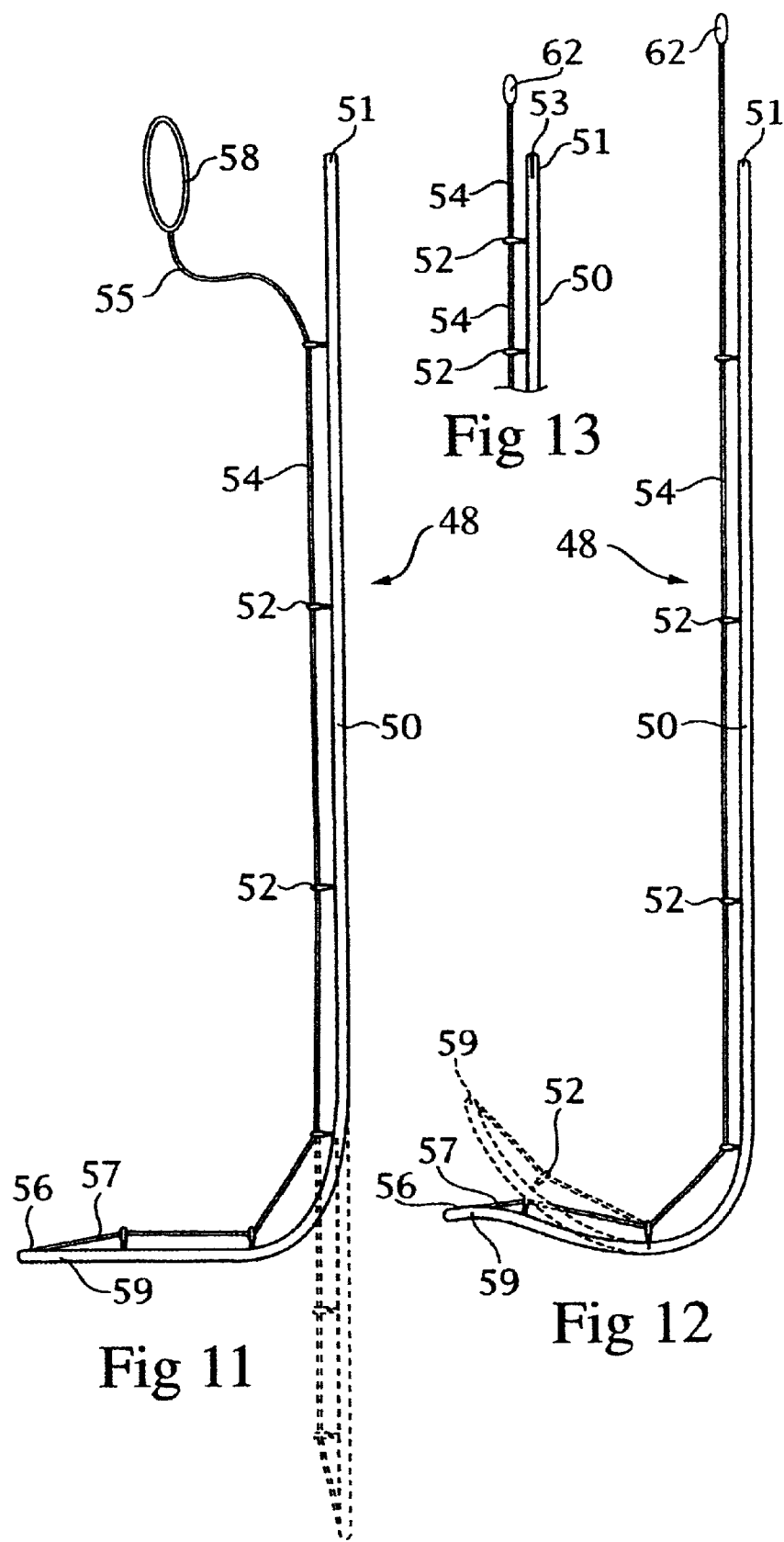

INTUBATION SYSTEM AND METHODS OF USE THEREOF

This invention relates to an intubation system and methods of use thereof, and particularly relates to an intubation system, which includes components such as an intubation slide and a directing guide wire assembly, and to methods of using the slide and the assembly. The invention further relates to a kit for containing the components of the intubation system.

BACKGROUND OF THE INVENTION

Basic cardio-pulmonary resuscitation (CPR) begins with the establishment and maintenance of an adequate airway. Physicians on a daily basis face situations which require tracheal intubation for airway management. Since there are many patients in which placing an endotracheal tube is extremely difficult to near impossible, many devices have been developed over the past 20 to 30 years to facilitate intubation in these patients. Each one of these devices has drawbacks. The American Society of Anesthesiologists has established a "difficult airway" algorithm, by which the above-noted many devices have attempted to achieve tracheal intubation. However, while each device has experienced limited success, failure of such devices has resulted, in many instances, in a surgical airway being necessitated by an incision in the neck and into the trachea. Furthermore, many of the devices may not be useful based on the design or clinical situation. The new intubation system of this invention combines multiple features to facilitate tracheal intubation. In addition, these multiple features allow the system to be used in almost any airway situation as opposed to the devices currently on the market which present deficiencies of one kind or another.

Prior Art United States Patents Cited

Frankel (U.S. Pat. No. 4,825,858) teaches flexible guides for an endotracheal tube. However, based on anatomy, this is essentially a guide into the esophagus, in which the endotracheal tube apparently follows its course into the mouth, then disengages at the level of the larynx. Further, the patent does not have the esophageal obturator; therefore, tube will enter the esophagus. Secondly, the potential exists for aspirating stomach contents since the airway is unprotected. In addition, Frankel lacks an intubating slide, and therefore no alignment with the vocal cord opening (glottis) is present; just blind endotracheal tube maneuvering. Frankel also lacks directing guide, accordingly there is no definitive line (i.e., guide) into the trachea.

Hedberg (U.S. Pat. No. 4,825,858) is directed to a stylet, similar to the directing guide of the herein disclosed invention, however, the Hedberg stylet is different in that the stylet has suction ports which are not needed and impractical. Further, the Hedberg stylet lacks a directing guide monofilament line to assist alignment with glottis. Overall, Hedberg 1) lacks an esophageal obturator, therefore this airway is unprotected from vomited stomach contents, and lack of esophageal blockage can cause the stylet to end up in esophagus; 2) further lacking an intubating slide, does not allow for tracheal alignment but only blind passage. Accordingly, this stylet may end up in the esophagus; essentially in the position of the esophageal obturator.

Ovassapian et al (U.S. Pat. No. 5,024,218) teaches an oropharyngeal airway adapted to facilitate tracheal intubation. The airway is designed to protect a fiberoptic endoscope from damage by the patient's teeth, and is distinct from the intubation device of this invention in that Ovassapian is for an oropharyngeal device which essentially holds the mouth open and is used to visualize the airway via fiberoptic camera. Blind passages of the endotracheal tube through this airway will end up in the esophagus, and not the trachea. To be effective Ovassapian requires visualization via a camera; the herein disclosed invention does not require fiberoptics.

Augustine (U.S. Pat. No. 5,042,469) teaches a tracheal intubation guide comprising a tubular member having a curved forward end shaped to follow the curvature of the back of the tongue and throat of a patient, and a rear end for projecting out through the mouth of the patient, and an anterior guide surface extending along at least part of the length of the member to its forward end for guiding the member into the throat into a position opposite the opening into the larynx. The tubular member has a through bore for holding an endotracheal tube, and the guide surface has a forward edge of concave shape for engaging the front of the epiglottis and seating over the hyoepiglottic ligament when the member is accurately positioned. This device is essentially an enclosed laryngoscope which is used routinely to intubate. The Augustine device adds no real advantage in either an easy or difficult airway since it can end up being positioned anywhere in the posterior pharynx. The abstract states "correct positioning can be detected by external palpation of the neck". This is virtually impossible in patients with large necks such as patients who are morbidly obese. It is for this difficult airway patient that the airway intubation system of this invention has been developed.

Parker (U.S. Pat. No. 5,174,283) teaches a device to facilitate rapid, accurate, blind access to the larynx or esophagus such as for emergency intubation of a patient's trachea and suctioning of the hypopharynx or esophagus. This guide is essentially a partially enclosed Ovassapian airway which lacks components of the esophageal obturator which protects from aspiration and prevents endotracheal tube passage into the esophagus.

Price (U.S. Pat. No. 5,353,787) teaches an oral airway to be used with an endotracheal tube along with inflatable balloon. This was a combination of two existing devices and does not allow proper alignment with the trachea since it lacks a slide which the herein disclosed invention embodies. Furthermore, it lacks both the esophagus obturator which leaves the airway "unprotected" and also lacks a directing guide to facilitate tracheal intubation. Lacking the directing guide and attempting to blindly place the larger endotracheal tube through the vocal cords becomes much more difficult, if not impossible.

Heinen, Jr. (U.S. Pat. No. 5,372,131) is for a multilumen intratracheal tube device. An inflation cuff is also taught. This device is not an emergency intubating device, but an endotracheal tube with a suction port.

Christopher (U.S. Pat. No. 5,694,929) teaches a mask with an additional port to assist with directly visualized fiberoptic guided intubation.

Gomez (U.S. Pat. No. 6,053,166) teaches an intubating assembly for positioning an intubation tube. This hinged device add an additional unnecessary step during an emergency. Furthermore, this device lacks the esophageal obturator and directing guide.

In summary, none of the prior art patents cited shows the unique intubation system of this invention; namely, the esophageal obturator, the intubating slide and the directing guide. Using one or more of the components of the intubation system will allow for the fool-proof placement of the endotracheal tube.

SUMMARY OF THE INVENTION

An object of this invention is to produce a system for efficiently intubating the airway, especially under emergency conditions and in situations involving "difficult airway" patients.

A further object of this invention is to intubate the airway without accidentally intubating the esophagus.

With these and other objects in mind, this invention contemplates an intubation system which includes a directing guide wire assembly having an end portion positionable in the trachea of a patient, an intubation slide for directing the end portion of the directing guide wire assembly toward the trachea, and an airway tube having an end portion positionable over and guidable by the directing guide wire assembly into the trachea.

In addition, this invention contemplates a directing guide wire assembly which includes a directing guide wire having a flexible end portion, a filament attached at one end thereof to the flexible end portion of the directing guide wire at a distal end thereof, and means for mounting the filament for movement relative to the directing guide wire to bend the flexible end portion of the directing guide wire upon forcible movement of the filament in a direction toward a proximal end of the directing guide wire.

Further, this invention contemplates a directing guide wire in a normally straight orientation, formed with a flexible end portion which is bendable from the normally straight orientation. An intubation slide is formed with a flexing angular bend having a guide path for guiding the flexible end portion through the angular bend to bend the flexible end portion.

Still further, this invention contemplates a kit formed by two joinable shell sections with pre-shaped nests for containing an intubation system including an intubation slide, a directing guide wire assembly and an airway tube.

Also, this invention contemplates a method of intubating the airway of a patient including the steps of applying an intubation slide within the mouth of the patient in alignment with the trachea of the patient, moving an end portion of a directing guide wire guidingly over the intubation slide and into the trachea, and moving an end portion of an airway tube guidingly over the directing guide wire and the end portion thereof.

A third object of this invention is to initially secure the esophagus with the obturator; thus, greatly reducing, if not eliminating, the risk of gastric aspiration.

These and other objects of the present invention will become apparent from a reading of the following specification taken in conjunction with the enclosed drawings.

BRIEF DESCRIPTION OF THE DRAWINGS

FIG. 3 is perspective view showing an intubation slide having an elongated shaft with a handle at a proximal end thereof and an angled foot at a distal end thereof with a generally U-shaped channel formed in a front of the shaft and the foot, all in accordance with certain principles of the invention;

FIG. 4 is a perspective view showing the intubation slide of FIG. 3 in accordance with certain principles of the invention;

FIG. 7 is an enlarged sectional view taken along line 7—7 of FIG. 6 showing the shaft and U-shaped channel of the intubation slide of FIG. 3 in accordance with certain principles of the invention;

FIG. 8 is a sectional view taken along line 8—8 of FIG. 6 showing an alternate embodiment of the intubation slide of FIG. 3 wherein a longitudinal groove is formed in a rear of the shaft of the intubation slide in accordance with certain principles of the invention;

FIG. 9 is a sectional view taken along line 9—9 of FIG. 5 showing the foot and the U-shaped channel of the intubation slide of FIG. 3 in accordance with certain principles of the invention;

FIG. 10 is a sectional view taken along line 10—10 of FIG. 5 showing the alternate embodiment of the intubation slide of FIG. 8 wherein the longitudinal groove continues and is formed in a rear of the foot of the intubation slide in accordance with certain principles of the invention;

FIG. 11 is a side view showing a directing guide wire assembly of the intubation system having a directing guide wire in a normally straight orientation with a flexible end portion at the distal end thereof, a plurality of eyelets spatially mounted along one side thereof, a filament attached to the distal end and threaded through the eyelets and extending to a proximal end of the directing guide wire, and a finger loop at a proximal end of the filament, all in accordance with certain principles of the invention;

FIG. 12 is a side view of the directing guide wire assembly of FIG. 11 showing the flexible end portion of the directing guide wire being bent at an angle from the normally straight orientation in accordance with certain principles of the invention;

FIG. 13 is a partial side view showing an alternate embodiment of the directing guide wire assembly where the proximal end of the directing guide wire is formed with a slit-notch for receipt of the proximal end of the filament in accordance with certain principles of the invention;

DETAILED DESCRIPTION OF THE INVENTION

Figures 1, 2:
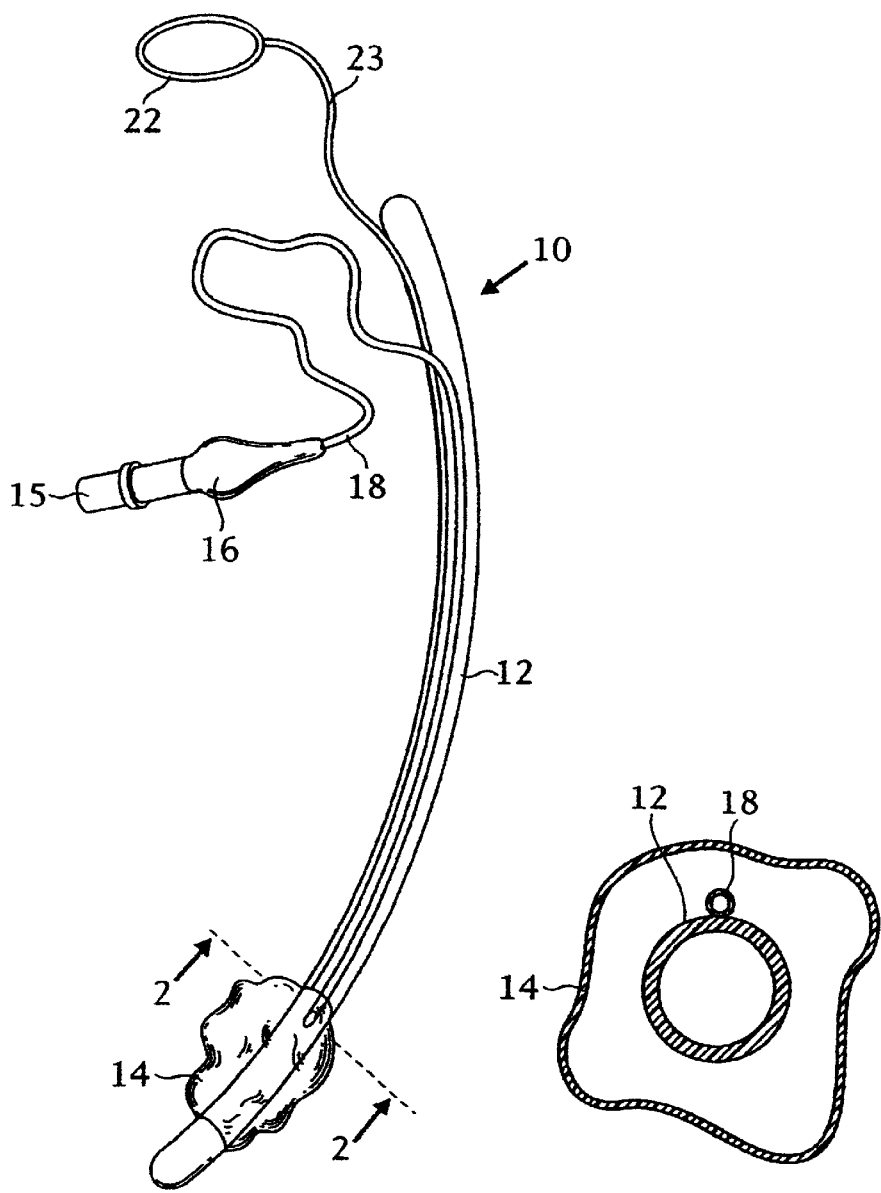
FIG. 1 is a perspective view showing an esophageal obturator which is used with the intubation system.
FIG. 2 is a sectional view taken along line 2—2 of FIG. 1 showing a ventilation tube, an inflatable balloon and an inflation tube of the esophageal obturator of FIG. 1.

With reference to FIGS. 1 and 2, an esophageal obturator 10 has a sealed tube 12, an esophageal occlusion balloon 14, a valve 15, a test or pilot balloon 16, an inflation tube 18 and a pull ring 22 on a retraction wire 23. The main function of the esophageal obturator 10 and its occlusion balloon 14 is to seal the esophagus of a patient prior to the process of inserting an airway tube 60 (FIG. 14) into the throat E (FIG. 14) of the patient. Pull ring 22 is for removing the esophageal obturator 10 from the patient's throat E when the obturator is no longer needed. The valve 15 and the balloon 16 are conventional in the art. The balloon 14 is filled with air through the valve 15 and the tube 18, by using a syringe inserted into the valve, and the balloon 16 is inflated simultaneously with the balloon 14 to indicate that the balloon 14 is also inflated.

Figure 18:
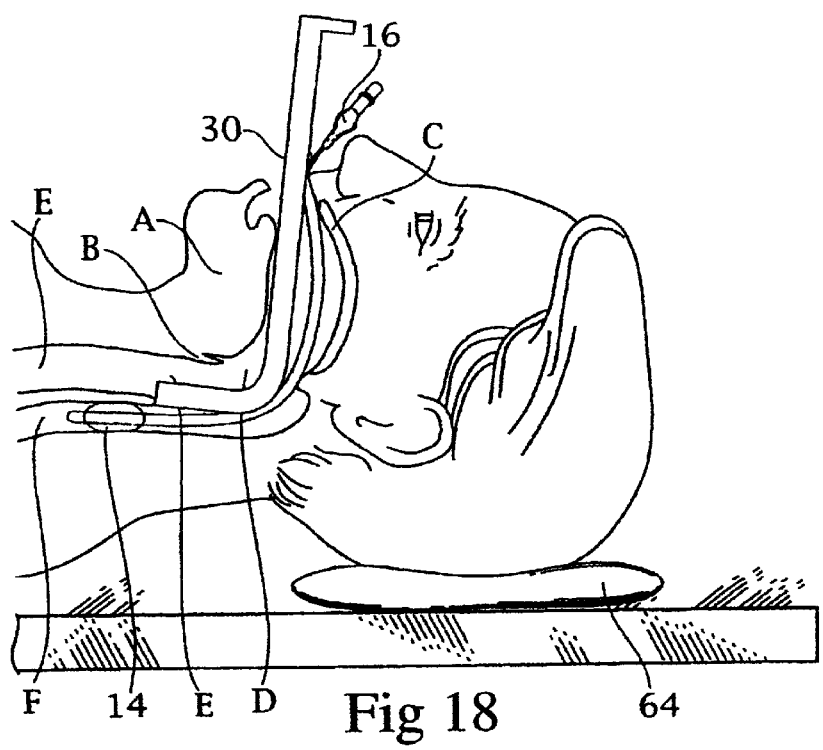
FIG. 18 is a side view showing the patient's upper anatomy of FIG. 16 with the esophageal obturator of FIG. 1 and the intubation slide of FIG. 3 in place in accordance with certain principles of the invention.
Figure 19:
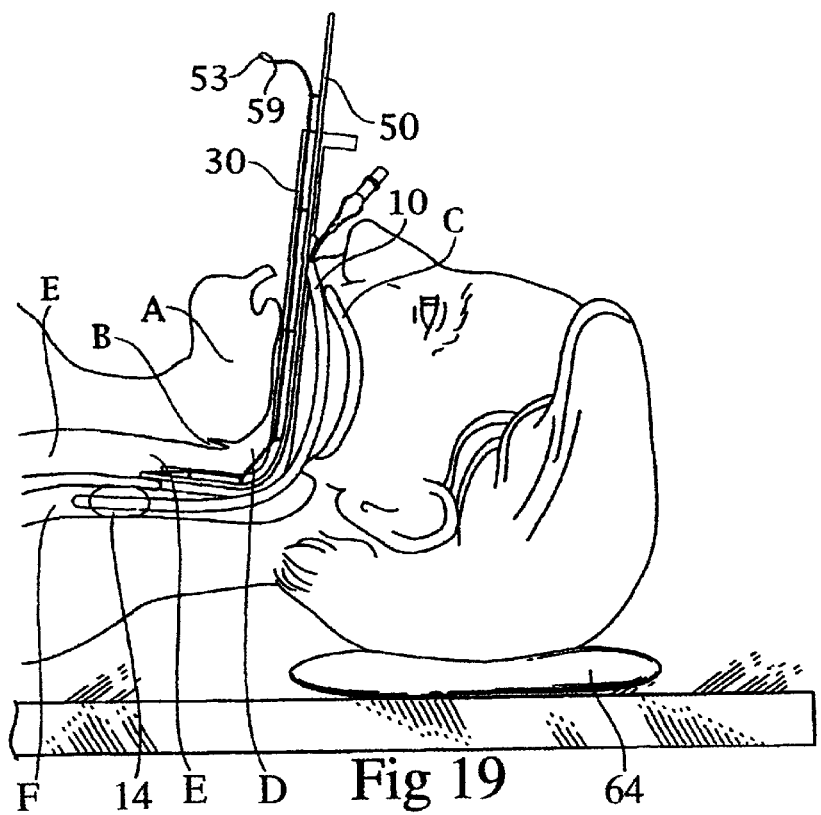
FIG. 19 is a side view showing the patient's upper anatomy of FIG. 16 with the esophageal obturator of FIG. 1, the intubation slide of FIG. 3 and the directing guide wire assembly of FIG. 11 in place in accordance with certain principles of the invention.

FIGS. 3 through 10 illustrate an intubation slide 30 which has a shaft 32 extending along an intermediate portion of the slide, with a foot 34 at a distal end 35 of the slide and a handle 36 at a proximal end 37 of the slide. The foot 34 and the handle 36 extend angularly in opposite directions from the shaft 32, with a flexing angular bend 33 being formed at a juncture between the shaft and the foot. A generally U-shaped channel 38 (FIGS. 7 and 9) forms a guide path in a first longitudinal section or front of the shaft 32 of the intubation slide 30 and extends from the proximal end 37 of the slide, through the bend 33, and continues through a top of the foot 34 at the distal end 35 of the slide. A longitudinal groove 40 (FIGS. 8 and 10) is formed in a second longitudinal section or rear of the shaft 32 of the intubation slide 30, which is opposite the first longitudinal section thereof. The groove 40 extends from the proximal end 37 of the slide to, and continues through, a bottom of the foot 34, which is opposite the top thereof, at the distal end 35 of the slide. The groove 40 is formed in the shaft 32 and the foot 34 to receive at least portions of the tube 12 of the esophageal obturator 10 as shown in FIGS. 18 and 19.

As illustrated in FIG. 11, a directing guide wire assembly 48 includes a directing guide wire 50, and also includes a plurality of spaced eyelets 52, which are attached to the directing guide wire 50 along its length between a proximal end 51 and a distal end 59 thereof. Further, the assembly 48 includes a filament 54, which is threaded through the eyelets 52, with a distal end 57 of the filament fixedly attached to a foot 56 at the distal end 59 of the directing guide wire 50. A finger ring 58 is attached to a proximal end 55 of the filament 54 adjacent the proximal end 51 of the directing guide wire 50.

In the context of the directing guide wire assembly 48, the filament 54 provides a means for flexing a flexible end portion of the directing guide wire 50. Further, the eyelets 52 provide a means for mounting the means for flexing, i.e., the filament 54, for movement relative to the directing guide wire to bend the flexible end portion of the directing guide wire 50 upon forcible movement of the means for flexing in a direction toward the proximal end 51 of the directing guide wire. The eyelets 52 further provide a means for maintaining the means for flexing, i.e., the filament 54, in a position adjacent the directing guide wire 50 between the distal end 59 and the proximal end 51 of the directing guide wire.

Figure 14:
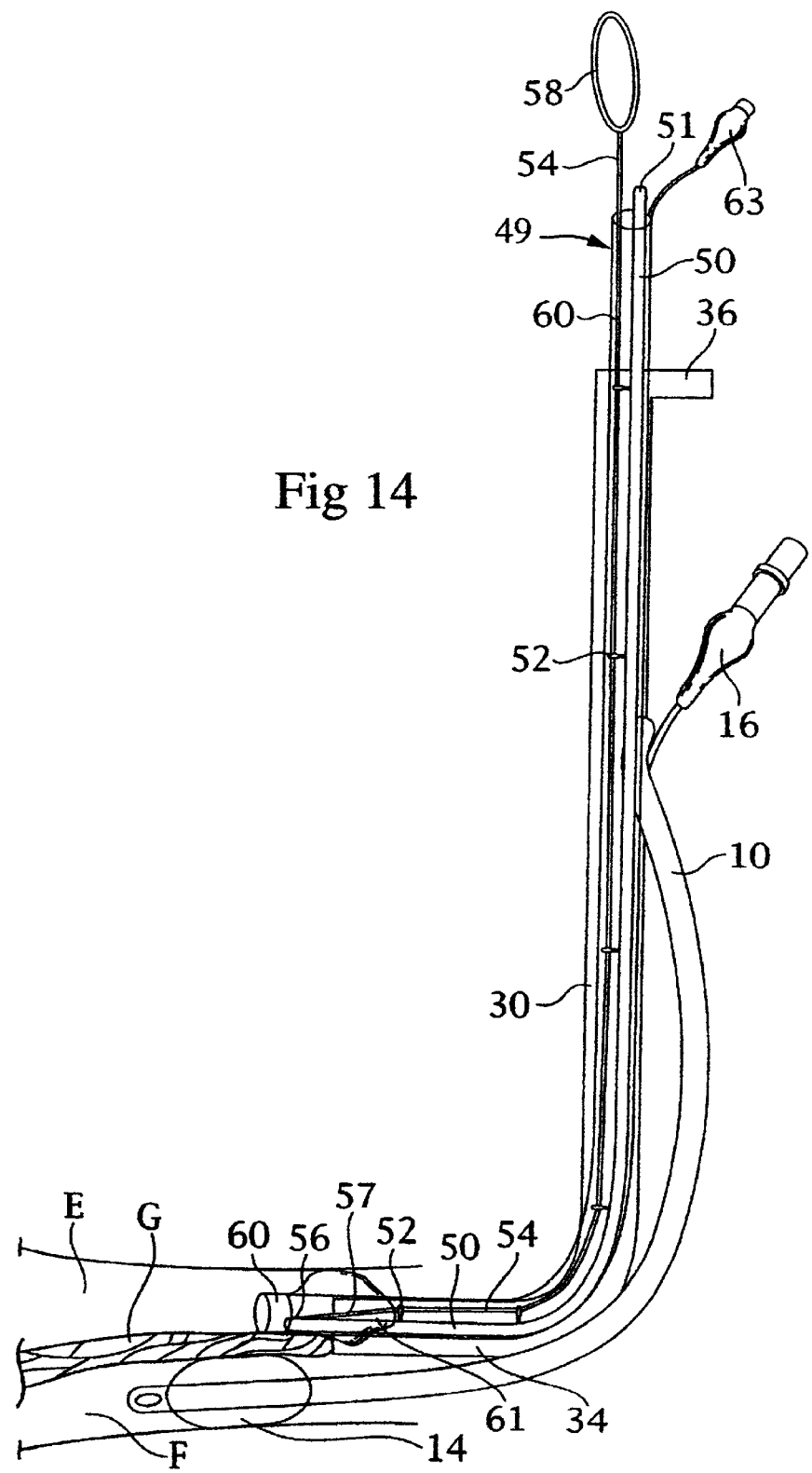
FIG. 14 is a side view showing the components of the intubation system, including an airway tube, in assembly with the esophagus and trachea of the patient in accordance with certain principles of the invention.

When the directing guide wire assembly 48 is not in use, the directing guide wire 50 is in a normal straight orientation from the proximal end 51 through the distal end 59 thereof as illustrated in FIG. 11, with the flexible end portion being shown in dashed lines. Due to the flexibility of a flexible end portion at the distal end 59 of the directing guide wire 50, the distal end 59 can be selectively flexed to non-straight orientations by grasping the finger ring 58 (FIG. 11), or a finger ring 62 (FIG. 13), and pulling the filament 54, as shown in solid view in FIGS. 11 and 12, and in dashed lines in FIG. 12. This flexibility allows for the flexible end portion at the distal end 59 of the directing guide wire 50 to be flexed and manipulated to locate in the entrance to the trachea E as shown in FIG. 14, and as described below.

With reference to FIG. 13, an alternative embodiment of the directing guide wire assembly 48 is illustrated in which the taut filament 54 can be placed and held in a slit-notch 53 formed in the directing guide wire 50 at the proximal end 51 thereof. In this alternative embodiment, the flexible end portion at the distal end 59 of the directing guide wire 50 is flexed by using the finger loop 62 and pulling the filament 54 taut to allow the distal end 59 to be inserted into the trachea E prior to assembly with the airway tube 60. When the flexed distal end 59 of the directing guide wire 50 is in place in the trachea E, the taut filament 54 is placed in the slit-notch 53 to retain the flexed distal end 59 in the established flexed state within the trachea. Thereafter, as described below, the airway tube 60 can be inserted onto and over the directing guide wire assembly 48 with the distal end of the airway tube being guided into and located in the trachea E. The directing guide wire assembly 48 can then be removed from within the airway tube 60 by pulling the proximal end 51 of the directing guide wire 50 in a direction away from the patient's mouth C.

It is noted that the airway tube 60 is also in a normal straight orientation when not in use, and is flexible and temporarily bendable along its length, including at the distal end thereof.

Referring to FIGS. 11, 12 and 13, the eyelets 52 preferably are flexible to allow the airway tube 60 to be placed completely over the directing guide wire assembly 48. Also, as noted above, the filament 54 is attached to the foot 56 at the distal end 59 of the directing guide wire 50, is threaded through the eyelets 52 and has the finger rings 58 or 62 at the proximal end 55.

Figure 24:
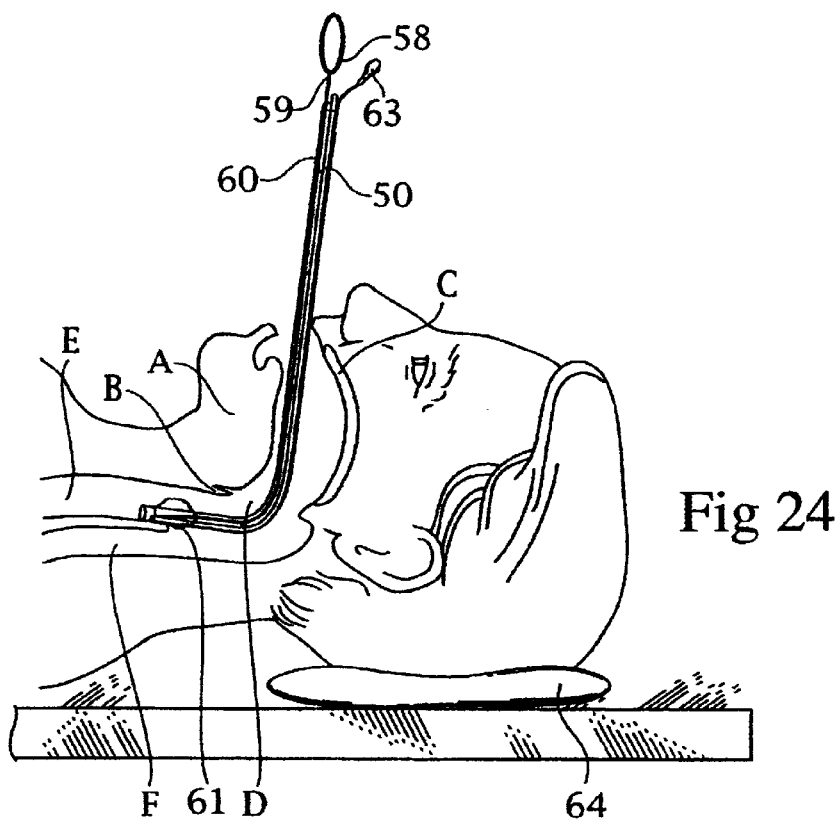
FIG. 24 is a side view showing the patient's upper anatomy of FIG. 16 with the airway tube of FIG. 14 located over the directing guide wire assembly of FIG. 11 to form a guide wire/airway tube subassembly in place in accordance with certain principles of the invention.
Figure 25:
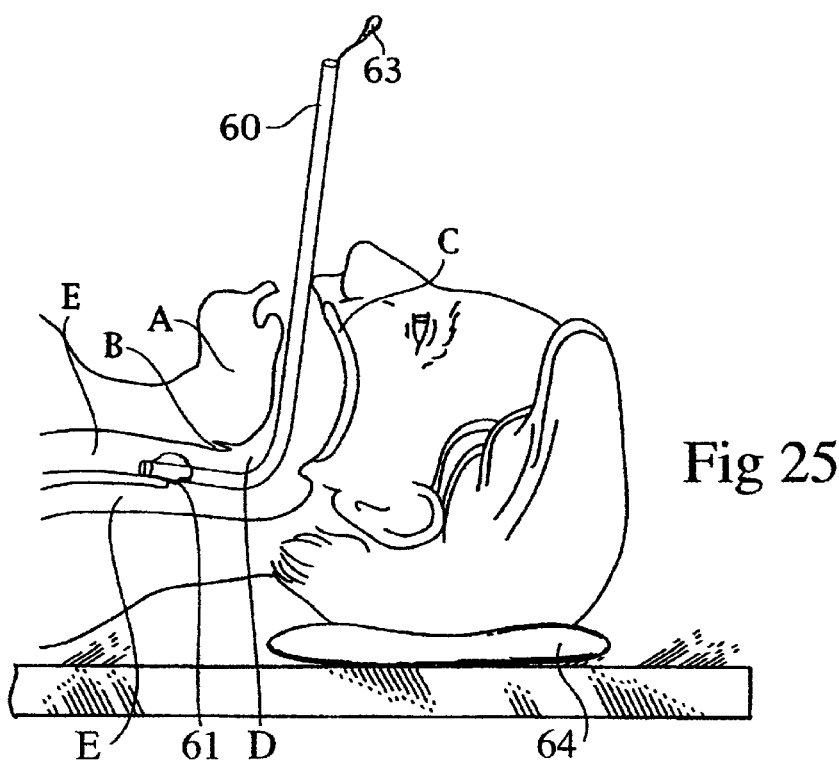
FIG. 25 is a side view showing the patient's upper anatomy of FIG. 16 with the airway tube of FIG. 14 in place, the directing guide wire assembly of FIG. 24 having been removed, in accordance with certain principles of the invention.
Figure 26:
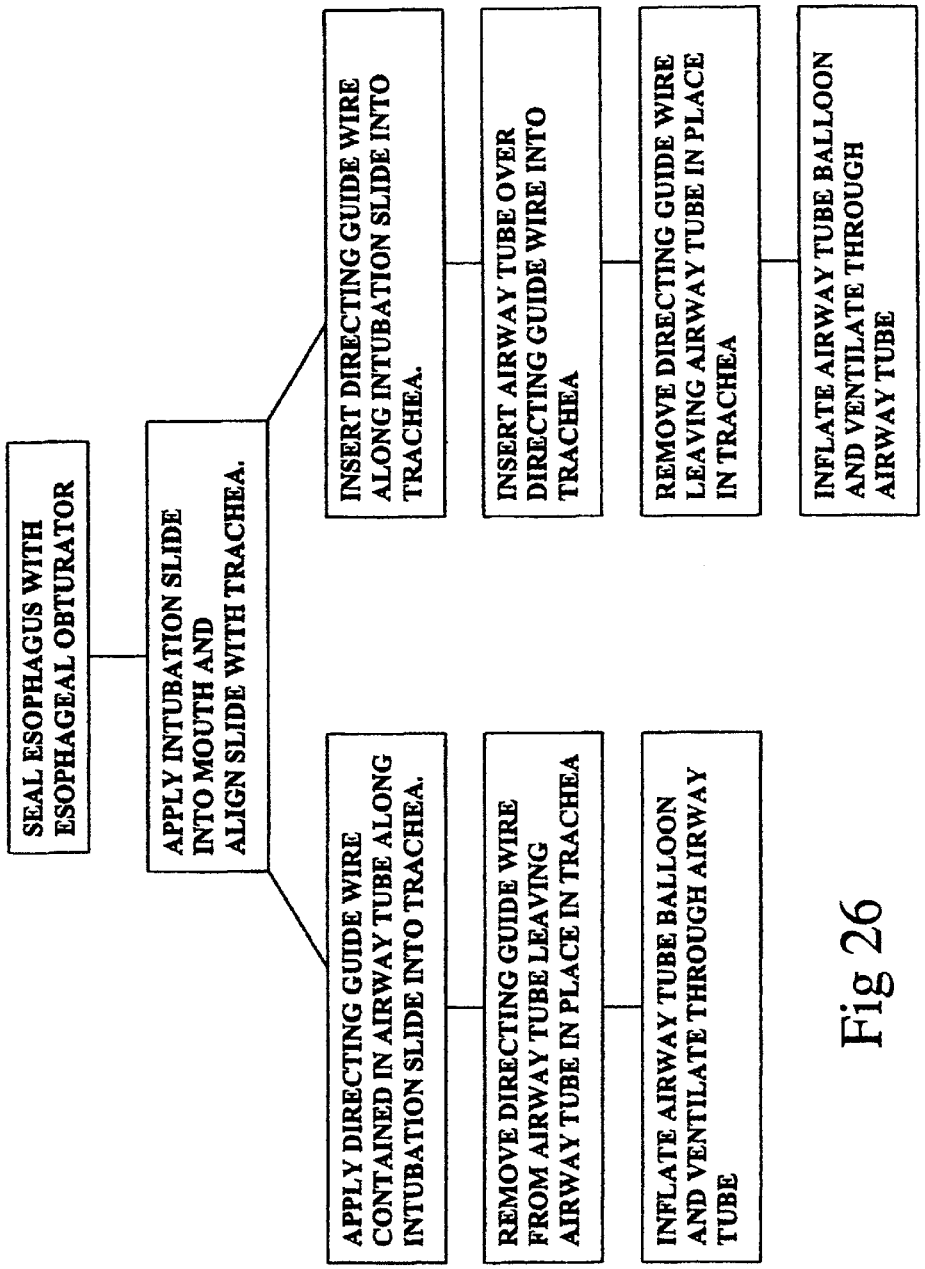
FIG. 26 is a flow chart depicting methods of using the intubation system.

In a first method of tracheal intubation, the airway tube 60, in the straight orientation, is placed over the directing guide wire assembly (FIGS. 14 and 24), also in the straight orientation, to form a guide wire/airway tube subassembly 49 (FIG. 14), also in the straight orientation. The distal end of a longitudinal side of the airway tube 60 of the subassembly 49, in the straight orientation, is located in the guide path in a portion of the U-shaped channel 38 of the intubation slide 30, which is contiguous with the shaft 32, at a location between the proximal end 37 and the angular bend 33. The distal end of the subassembly 49 is then moved within, and guided by, the channel 38 toward the angular bend 33.

As the distal end of the subassembly 49 is moved through the bend 33, the flexible end portion of the distal end 59 of the directing guide wire 50 is flexed from the straight orientation to the non-straight orientation as represented in solid line in FIG. 11. Since the distal end of the airway tube 60 is positioned over the distal end 59, the distal end of the airway tube is also flexed to the non-straight orientation.

Figure 20:
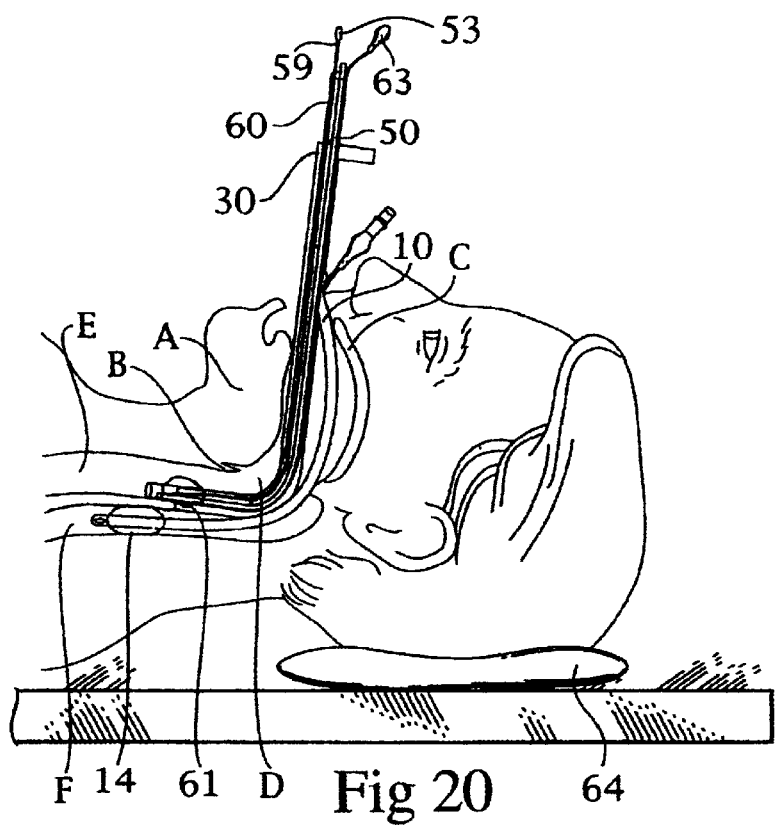
FIG. 20 is a side view showing the patient's upper anatomy of FIG. 16 with the esophageal obturator of FIG. 1, the intubation slide of FIG. 3, the directing guide wire assembly of FIG. 11 and the airway tube of FIG. 14 in place in accordance with certain principles of the invention.

In this manner, the distal end of the subassembly 49, having been inserted through the mouth C, is eventually guided by the U-shaped channel 38 from the angular bend 33 and into the foot 34 of the intubation slide 30 toward the trachea E, to insure that the distal end of the airway tube 60 is located for unfettered entry into the trachea E. The distal end of the subassembly 49, which includes the distal end 59 of the directing guide wire 50 and the distal end of the airway tube 60, is now properly located within the trachea E, as shown in FIG. 20. The directing guide wire assembly 48 can now be removed through the mouth C and from assembly with the airway tube, which remains in place as shown in FIG. 21, to provide an unobstructed airway for ventilation of the patient (FIG. 21)

Figure 21:
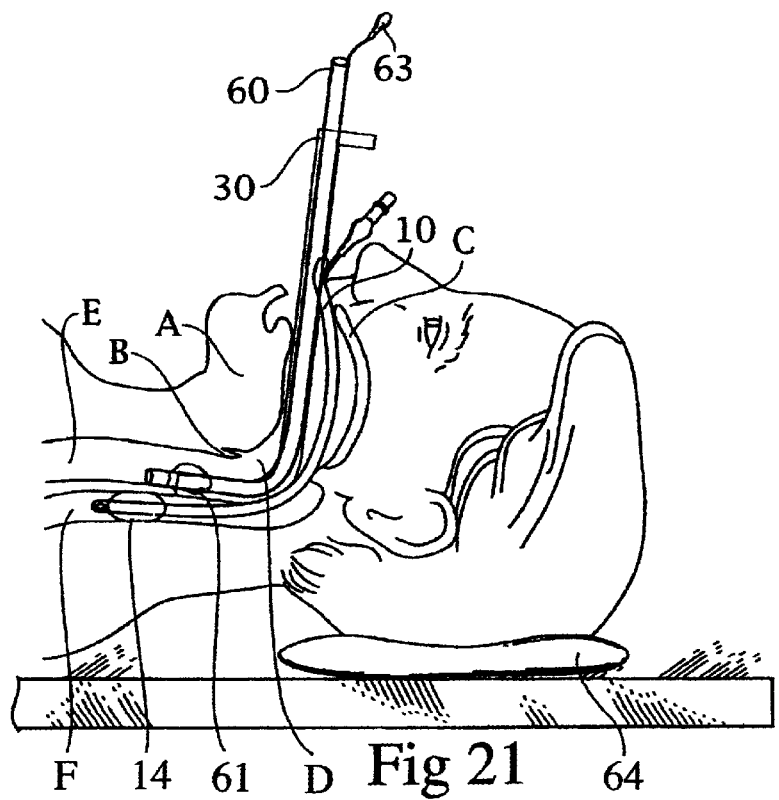
FIG. 21 is a side view showing the patient's upper anatomy of FIG. 16 with the esophageal obturator of FIG. 1, the intubation slide of FIG. 3 and the airway tube of FIG. 14 in place, the directing guide wire assembly of FIG. 11 having been removed, in accordance with certain principles of the invention.
Figure 22:
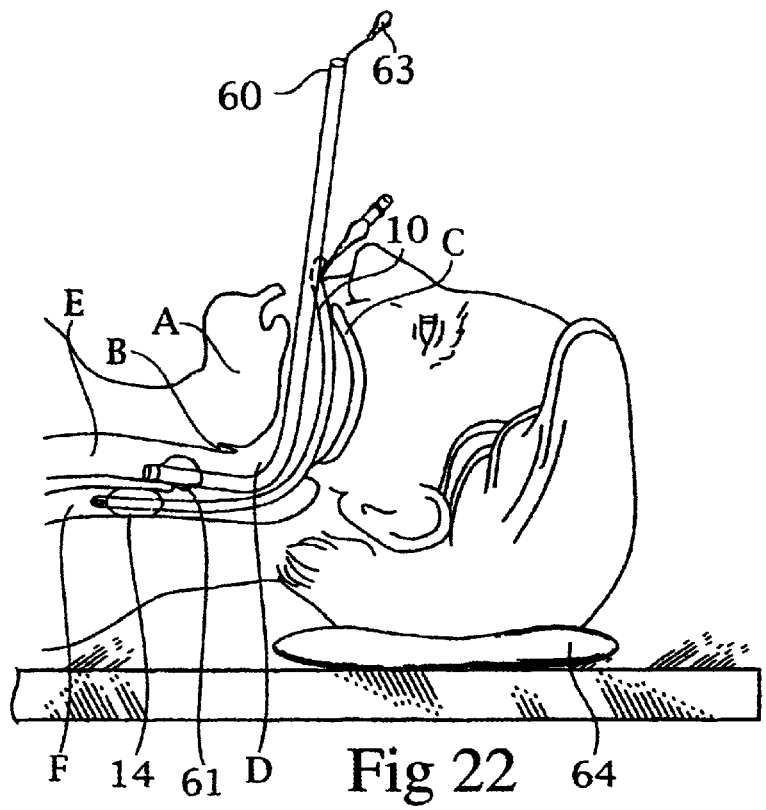
FIG. 22 is a side view showing the patient's upper anatomy of FIG. 16 with the esophageal obturator of FIG. 1 and the airway tube of FIG. 14 in place, the intubation slide of FIG. 3 and the directing guide wire assembly of FIG. 11 having been removed, in accordance with certain principles of the invention.
Figure 23:
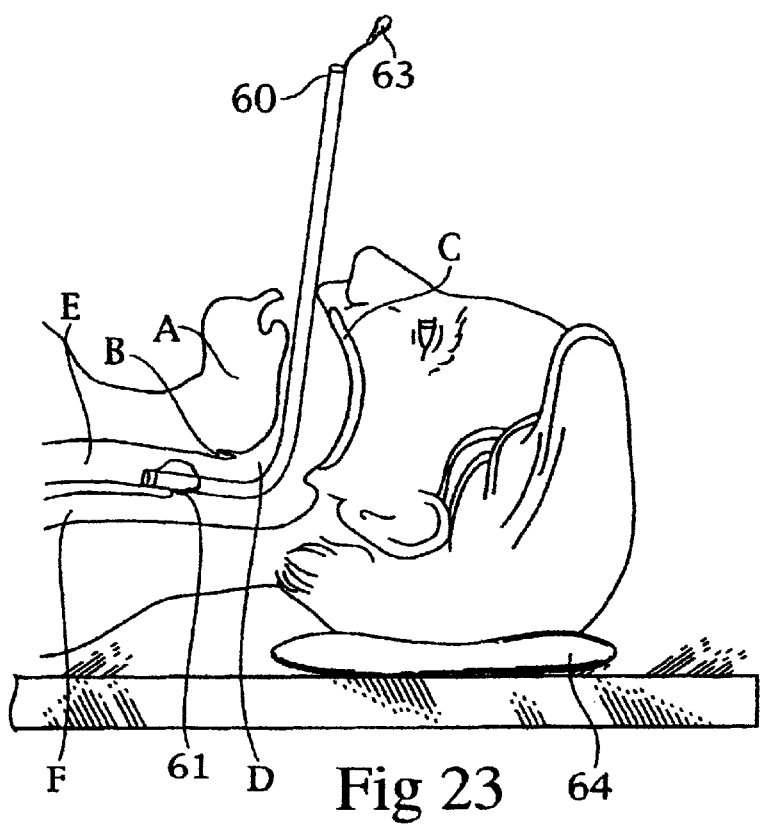
FIG. 23 is a side view showing the patient's upper anatomy of FIG. 16 with the airway tube of FIG. 14 in place, the esophageal obturator of FIG. 1, the intubation slide of FIG. 3 and the directing guide wire assembly of FIG. 11 having been removed, in accordance with certain principles of the invention.

As shown in FIGS. 19, 20 and 21, in a second method of tracheal intubation, the directing guide wire assembly 48, in the normally straight orientation and without the airway tube 60, is manipulated, in the manner described above, to move the flexible end portion at the distal end 59 of the directing guide wire 50 toward the trachea E (FIG. 19). In particular, the distal end 59 is moved through the portion of the channel 38, which is contiguous with the shaft 32, through the portion of the channel which is contiguous with the bend 33, and through the portion of the channel which is contiguous with the foot 34. As the distal end 59 of the directing guide wire 50 is moved through the portion of the channel 38 which is contiguous with the bend 33, the flexible end portion of the distal end is flexed to the non-straight orientation represented in solid line in FIG. 11, whereafter the now-flexed flexible end portion is moved into the portion of the channel in the foot 34, whereby the foot maintains the flexible end portion in the non-straight orientation.

During the intubation process, the distal end 59 of the wire 50 is guided toward the opening of the trachea E by employing the U-shaped channel 38 of the intubation slide 30. The flexible end portion at the distal end 59 is then flexed in the manner described above to locate and emplace the distal end 59 in the trachea E. The airway tube 60 is then threaded over the emplaced directing guide wire assembly 48 (FIG. 20) to locate the distal end of the airway tube in the trachea E. Once the distal end of the airway tube 60 is in place in the trachea E, the directing guide wire assembly 48 can be removed by grasping and pulling the proximal end 51 of the directing guide wire 50 to withdraw the assembly 48, whereby the airway tube remains in place to provide an unobstructed airway for ventilation of the patient (FIG. 21).

Frequently, it is difficult to maneuver the flexible end portion of the distal end 59 of the directing guide wire 50 when attempting to locate the entrance to the trachea E (FIG. 16), solely by use of the intubation slide 30. This difficulty can be overcome by gently pulling on the finger ring 58, or 62, to place a pulling tension on the filament 54 and thereby flex the flexible end portion of the distal end 59 of the directing guide wire 50 to seek entrance into the trachea E. This action will result in flexing the flexible end portion of the distal end 59 of the directing guide wire 50 from the flexed position illustrated in solid in FIG. 11, which is representative of the flexing accomplished by the flexing angular bend 33 of the intubation slide 30, to the flexed position illustrated in solid line, or in dashed line, in FIG. 12, which is representative of the flexing accomplished by the pulling of the filament 54.

In the context of the intubation slide 30, the flexing angular bend 33 provides a means interposed between adjacent ends of the shaft 32 and the foot 34 for flexing the end portion of the directing guide wire 50.

Regarding the above-described second method where the directing guide wire assembly 48 is inserted first, without the airway tube 60, the proximal end 51 of the directing guide wire 50 is formed with the slit-notch 53 to receive and hold the end of the filament 54 so that the airway tube 60 can be inserted over the finger ring 62 (FIG. 12) and over the directing guide wire. In this instance, the finger ring 62 is sufficiently small and flexible to fit into the inside of the airway tube 60. Alternatively, the filament 54 does not have to be held in the slit-notch 53, but could be held, for example, by tape or the like.

In the first method, where the airway tube 60 and the directing guide wire assembly 48 are inserted together as the subassembly 49, the ring 58 can be larger and less flexible than the ring 62 used in the second method, where the directing guide wire assembly is inserted first and then the airway tube is inserted over the directing guide wire assembly.

With reference to FIGS. 14, 15 and 19 through 25, the airway tube 60 has a balloon 61 on its distal end to occlude the trachea and to attain more effective ventilation through the airway tube. Also, the airway tube 60 is supplied with a pilot or test balloon 63 similar to that employed by the esophageal obturator 10. After the distal end of the airway tube 60 has been positioned within the trachea E, as described above, the balloons 61 and 63 are inflated.

FIG. 14 shows the intubation system of the invention with the esophageal obturator 10, the intubation slide 30, the airway tube 60, which contains the directing guide wire assembly 48, being emplaced.

Figure 15:
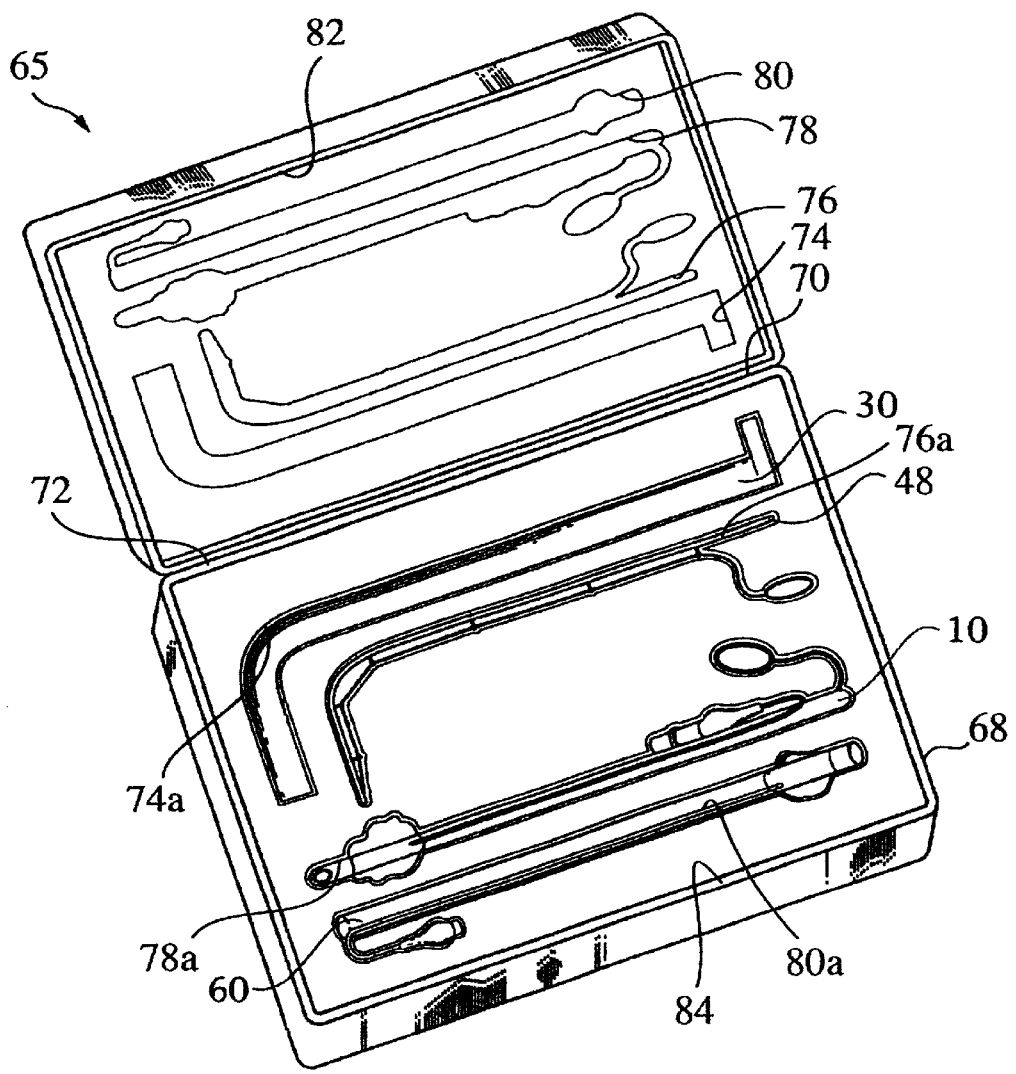
FIG. 15 is a perspective view showing a kit having two shell sections with nests for supporting the components of the intubation system in accordance with certain principles of the invention.

With reference to FIG. 15, there is shown a kit 65 containing the components of the intubation system of this invention. The components contained within the kit 65 include the esophageal obturator 10, the intubation slide 30, the directing guide wire assembly 48, including the directing wire guide 50, and the airway tube 60. The kit 65 is formed by two shell sections 66 and 68, which could be hinged along adjacent respective edges 70 and 72 to facilitate closure of one section upon the other section. The interior of each of the sections 66 and 68 is formed with respective pre-shaped nests 74, 76, 78 and 80, and 74a, 76a, 78a and 80a, which conform to the exterior shape of, and receive, respectively, the intubation slide 30, the directing guide wire assembly 48, the esophageal obturator 10, and the airway tube 60. The sections 66 and 68 are formed with respective mating edges 82 and 84, which could include facility for latching the edges together to maintain the kit in a closed condition.

Figure 16:
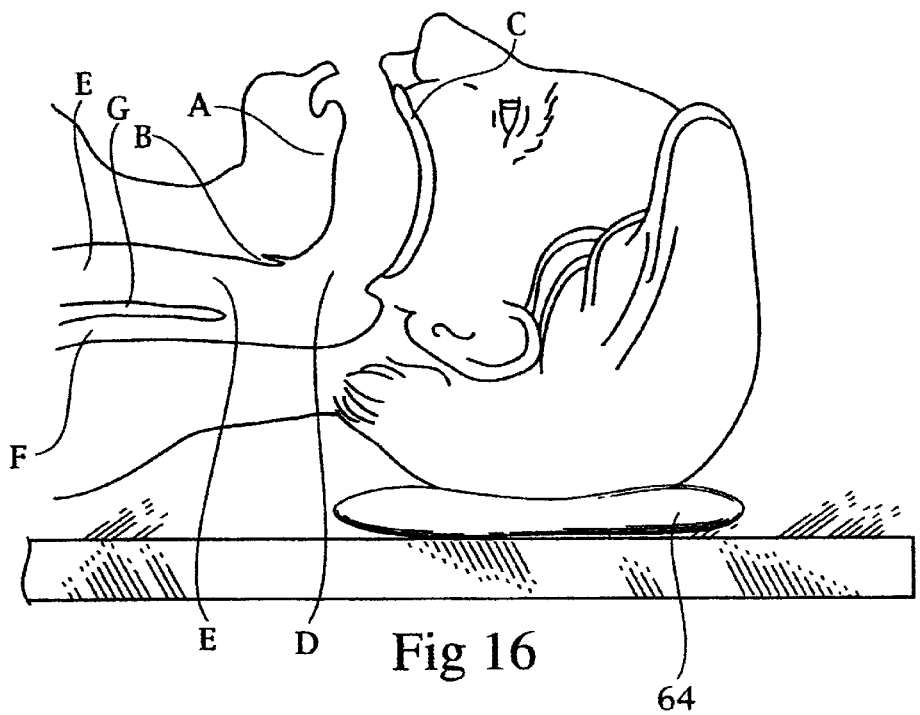
FIG. 16 is a diagrammatical view showing a representation of the patient's upper anatomy including the mouth, the throat, the epiglottis, the trachea and the esophagus.
Figure 17:
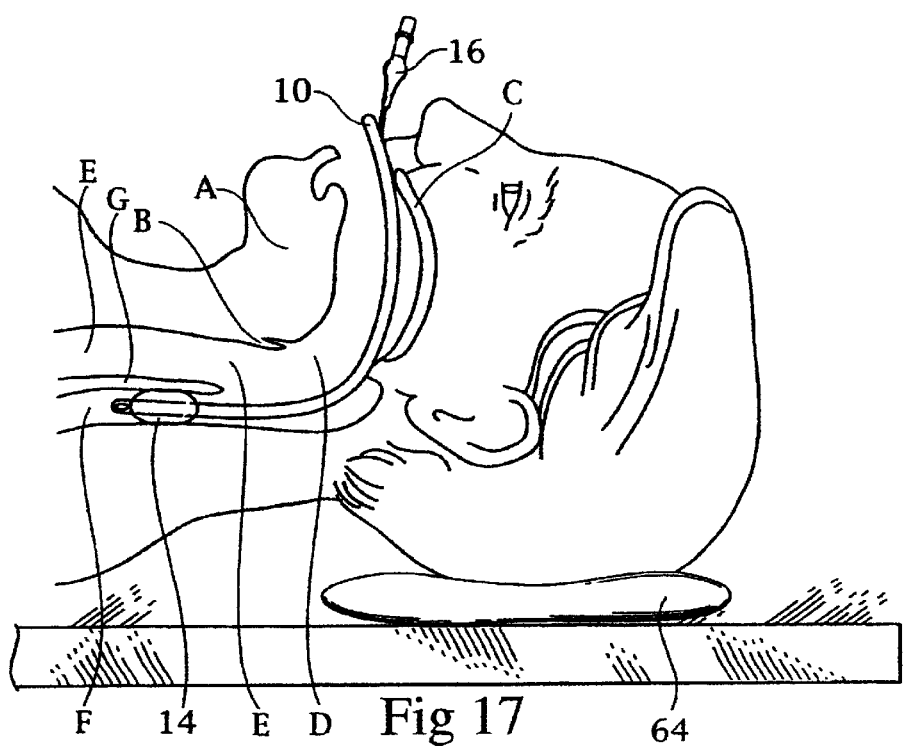
FIG. 17 is a side view showing the patient's upper anatomy of FIG. 16 with the esophageal obturator of FIG. 1 in place.

With reference to FIG. 16, there is shown a diagrammatic representation of the patient's anatomy in which the intubation system of this invention is used. The esophagus F is to be occluded by the esophageal obturator 10, and the corniculus or dividing wall G separates the esophagus F from the trachea E. Further in the diagrammatic representation of the anatomy, there is illustrated the tongue A, the epiglottis B, the mouth C and the throat D.

For the comfort of the patient, a pillow 64 is placed under the head of the patient.

The directing guide wire 50 is approximately 15 french (5 mm) in diameter, and 90 cm in length. The airway tube 60 can be placed over the directing guide wire assembly 48 from either the distal end 59 or the proximal end 51 of the directing guide wire 50, to form the guide wire/airway tube subassembly 49. When the distal end 59 of the directing guide wire 50, with or without the distal end of the airway tube 60, is guided through the channel 38 of the intubation slide 30, the flexible end portion of the directing guide wire will curve upward, as shown in solid line in FIG. 11, from the normal straight orientation as shown in dashed line, at the bend formed by the angular bend 33 at a juncture of the shaft 32 and the foot 34 of the intubation slide and come to rest in close proximity to the glottis (vocal cord opening). The operator, who is intubating the patient, will gently attempt to advance the directing guide wire 50 through the vocal cords. If any resistance is met, the operator will pull back slightly on the directing guide wire 50 and, with use of the filament 54, will pull back on the filament, for alignment of the distal end 59 of the directing guide wire 50 with the glottis where the distal end of the airway tube 60 can now thread over, and off, the distal end 59 and into the trachea E.

The esophageal obturator 10 is approximately 28 cm in length, 1.5 cm in diameter, and includes the sealed tube 12 with the distal inflatable balloon 14 and the proximal pilot balloon 16. In use, the mouth C of the patient is opened and the esophageal obturator 10 is placed blindly into the mouth C and advanced without resistance into the esophagus F. Once this occurs, the distal balloon 14 is inflated to further occlude the esophagus F. The obturator 10 confers the advantage of occluding the esophagus F in patients who are at risk of vomiting, aspirating and potentially dying as a result of tracheal intubation.

The current anesthesiology recommendations in all full-stomach patients at risk of aspiration (i.e.—trauma-related, pregnant, non-fasting, diabetics, bowel obstructions, obese, reflux or hiatal hernia) requires cricoid pressure (manual pressure on the anterior neck by a second operator in an effort to compress-close the esophagus). The reliability of the pressure procedure has been called into question since, probably, partly due to inexperienced personnel, performing the maneuver does not always effectively occlude the esophagus F. Another disadvantage is the requirement of a second person. By placing the esophageal obturator 10 first, we have accomplished the following:

1. Protection against aspiration.
2. Intra-esophageal, thus preventing the entering of the airway tube 60.
3. Does not require a second person.
4. Can be used itself with other currently existing devices in which cricoid pressure can distort the anatomy and hamper tracheal intubation.

The esophageal obturator 10 is not essential but its advantages make it desirable. Since the use of the esophageal obturator 10 is not an absolute requirement, it can be omitted if esophageal resistance is continually met, or if the patient suffers from an esophageal disease making its passage difficult or undesirable.

Figures 5, 6:
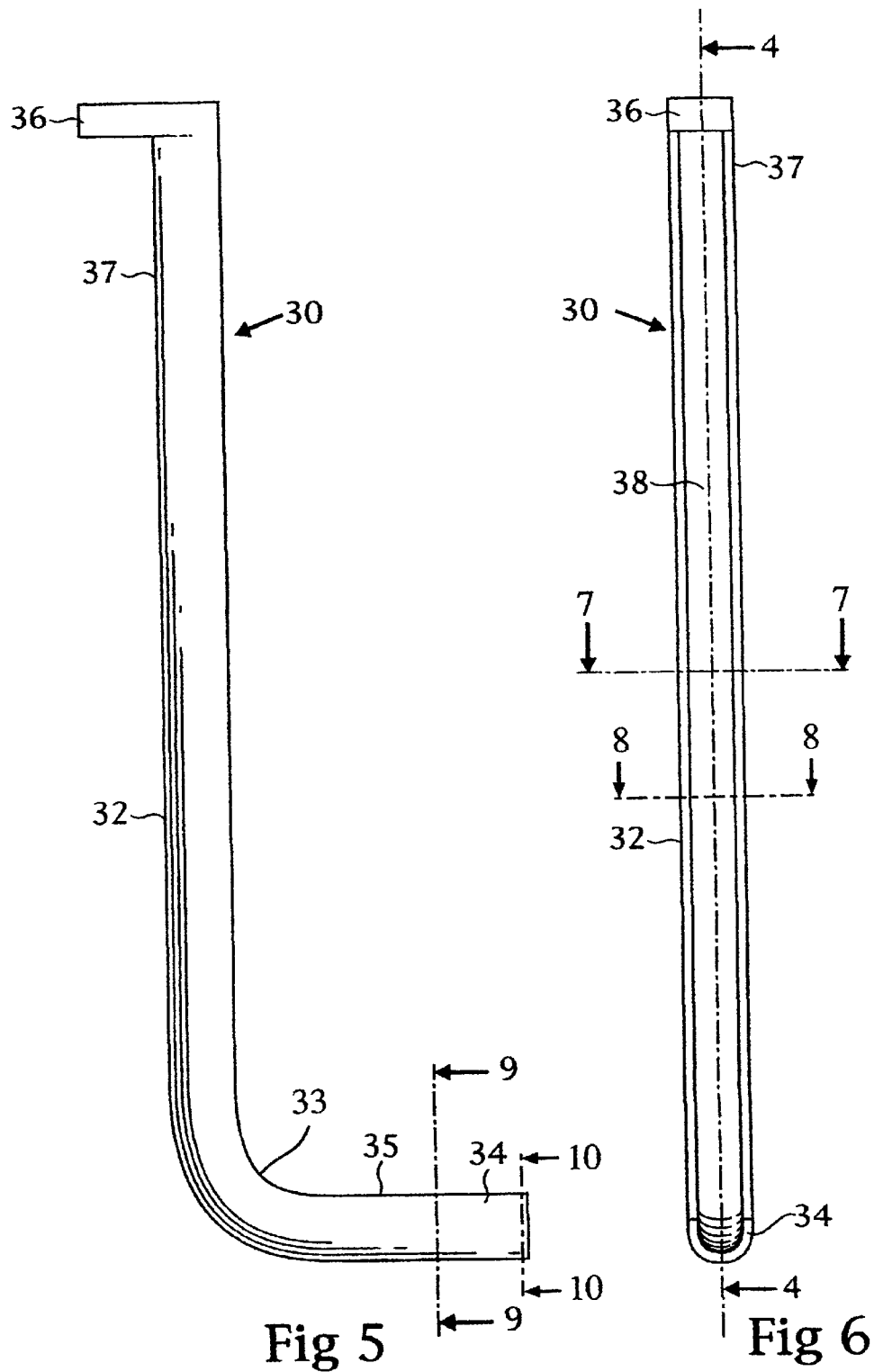
FIG. 5 is a side view showing the intubation slide of FIG. 3 in accordance with certain principles of the invention.
FIG. 6 is a front view showing the intubation slide of FIG. 3 in accordance with certain principles of the invention.

The shaft 32 of the intubation slide 30 is approximately 11 inches (28 cm) in length, the foot 34 is four inches (10 cm) in length, and is bendable at an angle from the shaft in a range from 90 degrees, as shown in FIGS. 4 and 5, to 130 degrees. The intubation slide 30 is formed generally in a half-circle cross section, as shown in FIGS. 7 and 8, with approximately three-fourths inch (2 cm) in diameter.

When the mouth C is opened, the intubation slide 30 is placed behind the tongue A and will rest in the posterior pharynx. The angled foot 34 should place the distal end 35 in close proximity to the glottis. The slide 30 can be maneuvered from side to side or front to back to improve its position, and to allow it to seat properly in front of the glottis.

As noted above, the foot 34 of the intubation slide 30 can be adjusted angularly between 90 degrees and 130 thirty degrees to facilitate alignment of the flexible end portion of the directing guide wire 50 with the opening of the trachea E. In order to accomplish this angular adjustment, at least the foot 34 is composed of a slightly malleable construction.

Operation of the Intubation System

STEP 1—Open mouth

2—Insert esophageal obturator 10—inflate balloon 14

3—Place intubation slide 30 into mouth

4—Place directing guide wire assembly 48 into intubation slide 30 with or without airway tube 60 and advance into trachea 5—Slide airway tube 60 past vocal cords, then inflate balloon 61, remove directing guide wire assembly 48

6—Confirm placement of airway tube 60

7—Remove intubation slide 30

8—Remove esophageal obturator 10

9—Ventilate patient through airway tube 60.

Table A outlines advantages and disadvantages of currently available airway and intubation devices. In Table B, the intubation devices of Table A are compared to the intubation system of this invention.

TABLE A

| | | |
|---|---|---|
| 1. LMA (Laryngael Mask Airway) | Internal mask in posterior oropharynx to ventilate | temporizing measure until endotrachael intubation does not protect airway from aspiration. airway protection requires cricoid pressure which can impede placement Poor seal, from anatomy/blood/secretions can make ventilation impossible |
| 2. Light Wand Lighted stylette | Tube placed over lighted stylette which is placed into mouth. Tube is advanced off stylette once illumination is seen on neck. | Requires darkened areas (impossible in daylight) Light may be in esophagus in thin patients Light may not be seen in obese patients. Requires tube to be placed at distal end at onset which when blindly maneuvered can produce bleeding/ trauma |

TABLE A-continued

| | | |
|---|---|---|
| 3. Combitube | Single tube with two lumens blindly placed and if in trachea (which rarely happens) acts as endotracheal tube. Intubates esophagus 90–95%+. Esophagus is occluded by tube which prevents aspiration but ventilation occurs through ports in tube at proximal end which should by default enter trachea. Proximal cuff which holds approximately 80 cc air inflated in oropharynx to prevent oxygen escape. | Large oropharyngeal balloon inflated can lead to esophageal rupture in predisposed patients Not tolerated if gag reflux is present Has certain height restrictions for usage Can have failure to ventilate with clogged ports from blood/secretions or with blood/secretions/broken teeth, etc. surrounding the vocal cords Does not protect from aspiration of blood from upper airway into lungs Temporizing measure until endotracheal intubation Should not be used in patients who have esophageal pathology or ingested caustics |
| 4. Esophageal Obturator Airway | Similar to Combitube but lacks ability to intubate trachea (albeit extremely low) | Has essentially been replaced by the Combitube |
| 5. Gum Elastic Bougie | Thin stylette placed into mouth with or without direct vision attempting to pass through vocal cords | Has no ability for redirection No airway protection Shorter length (~70 cm) can cause displacement into esophagus |
| 6. Lighted Fiberoptic Laryngoscopes | Both are rigid metal instruments that allow indirect viewing of the glottis using fiberoptic bundles | Very difficult to use "Serious commitment and training are needed to become comfortable with these devices" Anesthesia and Perioperative Complications, 2nd edition: J L Benumof, L. J. Saidman; Mosby; 1999 Attempts severely impaired due to poor vision from blood, secretions Would be completely useless in an emergency situation by minimally trained personnel. |

TABLE B

| Inventive Intubation System | Advantage/Principle Compared with Aforementioned Devices |
|---|---|
| vs. LMA | Not a temporizing measure but definitive Would protect from aspiration Can still be used with cricoid pressure |
| vs. Light Wand | Not dependent on ambient light Does not require visualization of light Tube can be placed after entering glottis |
| vs. Combitube | No height restrictions Not a temporizing measure but definitive airway Not dependent on port holes (which have potential to clog) Protects from aspirating blood |
| vs. Gum Elastic Bougie | Has a tract (intubating slide) to follow to improve success Has monofilament line for redirection Longer length to prevent slippage into esophagus |
| vs. Bullard upsher Laryngoscopes | A blind procedure which is not vision dependent Simple to use Not interfered with by blood/secretions |

Many advantages are attendant to the use of the intubation system of this invention. The endotracheal intubation system consists of three major components, the intubation slide 30, the directing guide wire assembly 48 and the airway tube 60, which are a welcome addition to the armamentarium of difficult airway treating devices available to assist in the establishment of a definitive airway. The quickest, easiest and most widely used method of tracheal intubation, prior to this invention, is direct laryngoscopy using a standard laryngoscope with various blades. Since this approach is difficult in many patients who have anatomical problems, failures occur using this basic technique. This problem prompted the design of laryngoscope blades or devices in order to facilitate tracheal intubation. Many of these "difficult airway devices" have also failed, ultimately requiring the technique of a surgical airway into the neck to establish tracheal intubation.

Each above-described component of the intubation system of this invention can be used individually with the standard direct vision laryngoscopic approach to facilitate intubation. The system of this invention is also designed to operate independently, and not require direct vision, or a second operator. The goal of the herein described invention is that the system become standard practice in every hospital, ambulatory center, and ambulance to assist the paramedic/physician/anesthetist with obtaining an airway. Since many paramedics are not allowed to perform surgical airways, and most anesthesiologists/physicians have never performed one (even in controlled situations), the intubation system, as described herein, offers an advantageous alternative to the surgical (or final) approach.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. Method of intubating an airway of a patient comprising the steps of:
 (1) sealing an esophagus of the patient with an esophageal obturator,
 (2) applying an intubation slide into a mouth of the patient to align the intubation slide with a trachea of the patient,
 (3) applying a directing guide wire having disposed thereon an airway tube, along a guide path of the intubation slide and into the trachea, and
 (4) removing the directing guide wire from the mouth of the patient to thereby provide an unobstructed airway allowing the patient to receive air or oxygen into the lungs.

2. Method of intubating an airway of a patient comprising the steps of:
 (1) sealing an esophagus of the patient with an esophageal obturator,
 (2) applying an intubation slide into a mouth of the patient to align the intubation slide with a trachea of the patient,
 (3) applying a directing guide wire along a guide path of the intubation slide and into the trachea,
 (4) inserting an airway tube over the directing guide wire and into the trachea, and
 (5) removing the directing guide wire from the mouth to thereby provide an unobstructed airway allowing the patient to receive air or oxygen into the lungs.

3. A directing guide wire assembly for facilitating the entry of an airway tube into a trachea of a patient comprising a directing guide wire having a length with a proximal end and a flexible distal end with a series of eyelets spaced along the length of the directing guide wire, with the eyelets receiving a filament having a distal end attached to the flexible distal end and is free at a proximal end thereof adjacent the proximal end of the directing guide wire, and when the filament is pulled back and forth, the distal end of the directing guide wire is flexed back and forth to facilitate the entry of the distal end of the directing guide wire into the trachea.

4. The directing guide wire assembly of claim 3 having disposed therewith an airway tube.

5. The directing guide wire assembly of claim 3 wherein the airway tube is inserted over the directing guide wire.

6. The directing guide wire assembly of claim 5 wherein a ring is attached to the proximal end of the filament.

7. An intubation system, which comprises:
   a directing guide wire assembly having an end portion positionable in a trachea of a patient;
   an intubation slide for directing the end portion of the directing guide wire assembly toward the trachea of the patient;
   an airway tube having an end portion positionable over the end portion of the directing guide wire assembly for guidance of the end portion of the airway tube into the trachea of the patient; and
   wherein the intubation slide comprises:
      a shaft having an end;
      a foot extending angularly from the shaft and having an end adjacent and spaced from the end of the shaft; and
      means interposed between the adjacent ends of the shaft and the foot for flexing the end portion.

8. The intubation slide as set forth in claim 7, wherein the means for flexing comprises:
   a flexing angular bend which joins with and links the shaft and the foot.

9. The intubation slide as set forth in claim 8, which further comprises:
   a channel formed in the shaft, the flexing angular bend and the foot for directing the end portion of the directing guide wire assembly toward the trachea.

10. The intubation slide as set forth in claim 7, which further comprises:
    at least the foot being composed of a malleable construction.

11. A directing guide wire assembly, which comprises:
    a directing guide wire having a flexible end portion,
    means for flexing the flexible end portion of the directing guide wire, and
    means for mounting the means for flexing for movement relative to the directing guide wire to bend the flexible end portion of the directing guide wire upon forcible movement of the means for flexing in a direction away from the flexible end portion.

12. The directing guide wire assembly as set forth in claim 11, wherein the flexible end portion is at a distal end of the directing guide wire, which further comprises:
    the directing guide wire formed with a proximal end opposite the distal end thereof; and
    means for maintaining the means for flexing in a position adjacent the directing guide wire and extending between the distal end and the proximal end of the directing guide wire.

13. The directing guide wire assembly as set forth in claim 12, which further comprises:
    the means for maintaining being formed by a plurality of eyelets which are mounted spatially on the directing guide wire between the distal end and the proximal end thereof.

14. The directing guide wire assembly as set forth in claim 11, which further comprises:
    the means for flexing being a filament attached at one end thereof to the flexible end portion of the directing guide wire.

15. The directing guide wire assembly as set forth in claim 14, wherein the flexible end portion is located at a distal end of the directing guide wire, and the one end of the filament is a distal end thereof, which further comprises:
    the directing guide wire formed with a proximal end opposite the distal end thereof;
    the filament formed with a proximal end opposite the distal end thereof; and
    a slit-notch formed in the proximal end of the directing guide wire for selective receipt of the proximal end of the filament.

16. An intubation system, which comprises:
    a directing guide wire formed in a normally straight orientation,
    the directing guide wire formed with a flexible end portion which is bendable from the normally straight orientation;
    an intubation slide; and
    means formed on the intubation slide for bending the flexible end portion of the directing guide wire into a non-straight orientation.

17. The intubation system as set forth in claim 16, which further comprises:
    an airway tube having an end portion positioned over the flexible end portion of the directing guide wire in the normally straight position and bendable with the flexible end portion of the directing guide wire into the non-straight orientation.

18. The intubation system as set forth in claim 16, which further comprises:
    an airway tube having an end portion being positionable over the flexible end portion of the directing guide wire when the flexible end portion is in the non-straight orientation.

19. A kit containing an intubation system, which comprises:
    two shell sections joinable to form an enclosure;
    first, second and third nests located in at least one of the two shell sections;
    an intubation slide located in the first nest;
    a directing guide wire assembly located in the second nest; and
    an airway tube located in the third nest.

20. The kit as set forth in claim 19, which further comprises:
    each of the first, second and third nests formed as a cavity which is complementary to at least a portion of an exterior configuration of the intubation slide, the directing guide wire assembly and the airway tube, respectively.

21. The kit as set forth in claim 19, which further comprises:
    a fourth nest; and
    an esophageal obturator located in the fourth nest.

* * * * *